United States Patent [19]

Jones

[11] Patent Number: 4,643,111
[45] Date of Patent: Feb. 17, 1987

[54] RESOURCE RECOVERY UTILITY

[76] Inventor: Robert L. Jones, 275 Brooks Rd., Bethany, Conn. 06525

[21] Appl. No.: 767,892

[22] Filed: Aug. 21, 1985

[51] Int. Cl.$^4$ ............................................. F23B 7/00
[52] U.S. Cl. ..................................... 110/234; 52/595; 71/10; 71/11; 110/223; 110/255; 210/901; 405/129; 405/284
[58] Field of Search .............. 110/218, 219, 223, 224, 110/227, 228, 233–235, 255; 405/128, 129, 53, 55, 284; 52/595; 71/10–12; 210/750–751, 603, 901; 48/111, 197 A

[56] References Cited

U.S. PATENT DOCUMENTS

| 3,563,044 | 2/1971 | Gerwick, Jr. ................. | 405/284 X |
| 3,647,405 | 3/1972 | Smith ........................... | 110/234 X |
| 3,805,715 | 4/1974 | Keller ........................... | 110/224 |
| 4,193,206 | 3/1980 | Maffet ........................... | 71/12 X |
| 4,269,562 | 5/1981 | Burgess ......................... | 405/129 X |
| 4,323,367 | 4/1982 | Ghosh ........................... | 210/603 X |
| 4,324,508 | 4/1982 | Hilfiker et al. ................ | 405/284 |
| 4,360,553 | 11/1982 | Landheer ...................... | 52/595 X |
| 4,483,641 | 11/1984 | Stoll ............................. | 405/129 |
| 4,518,399 | 5/1985 | Croskell et al. .............. | 55/16 |
| 4,531,463 | 7/1985 | Kratz et al. .................. | 110/219 X |

FOREIGN PATENT DOCUMENTS

| 3300464 | 7/1984 | Fed. Rep. of Germany ...... 405/129 |
| 2141732 | 1/1985 | United Kingdom ................ 210/603 |

OTHER PUBLICATIONS

Public Works, "From Dump to Fill to Recreational Site", p. 114, Feb. 1970.
Waste Age, "Geomembrane Liner Design", p. 27–30, Sep. 1982.

Primary Examiner—Henry C. Yuen
Assistant Examiner—Steven E. Warner
Attorney, Agent, or Firm—Kramer and Brufsky

[57] ABSTRACT

A resource recovery utility is provided comprising a landfill having a continuous wall surrounding the perimeter thereof and a containment structure extending completely over the landfill affixed to the continuous wall. Refuse can be introduced into the landfill and compacted therein and at least a portion of the compacted refuse can be removed therefrom. Methane generated by anaerobic bacterial digestion of organic materials contained in the refuse can be removed and recovered.

16 Claims, 5 Drawing Figures

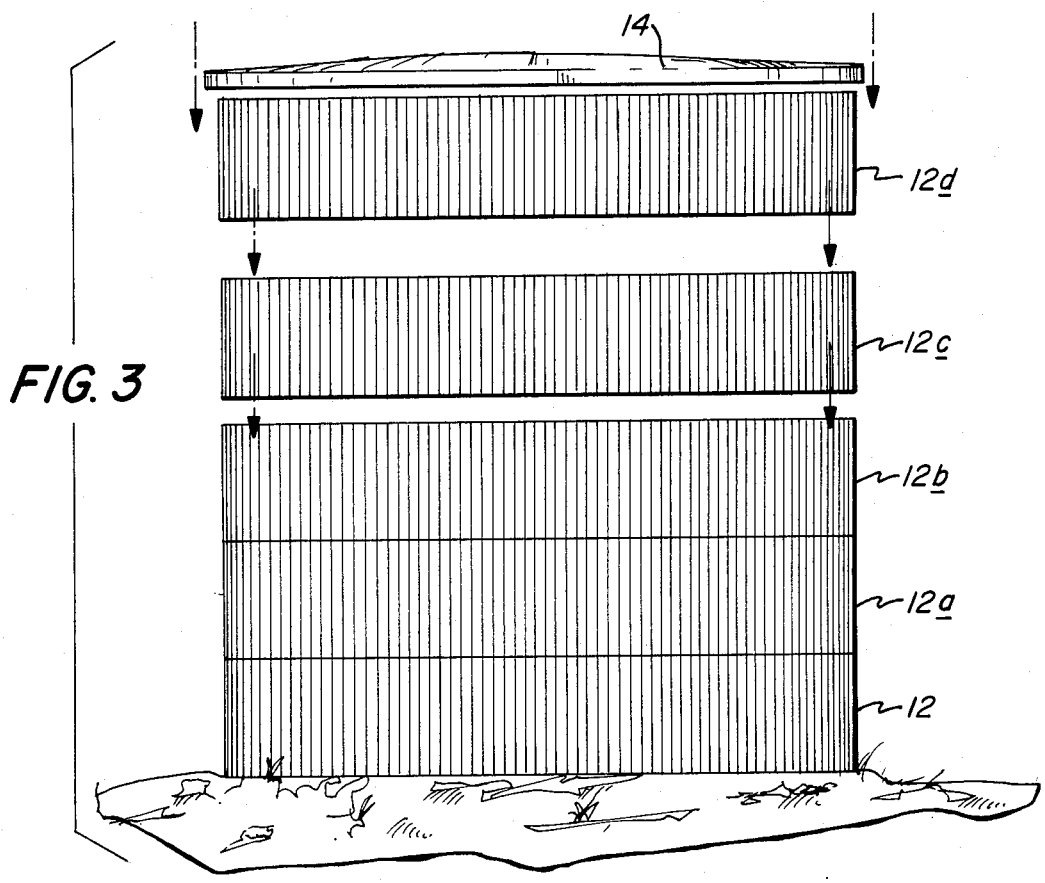
FIG. 3
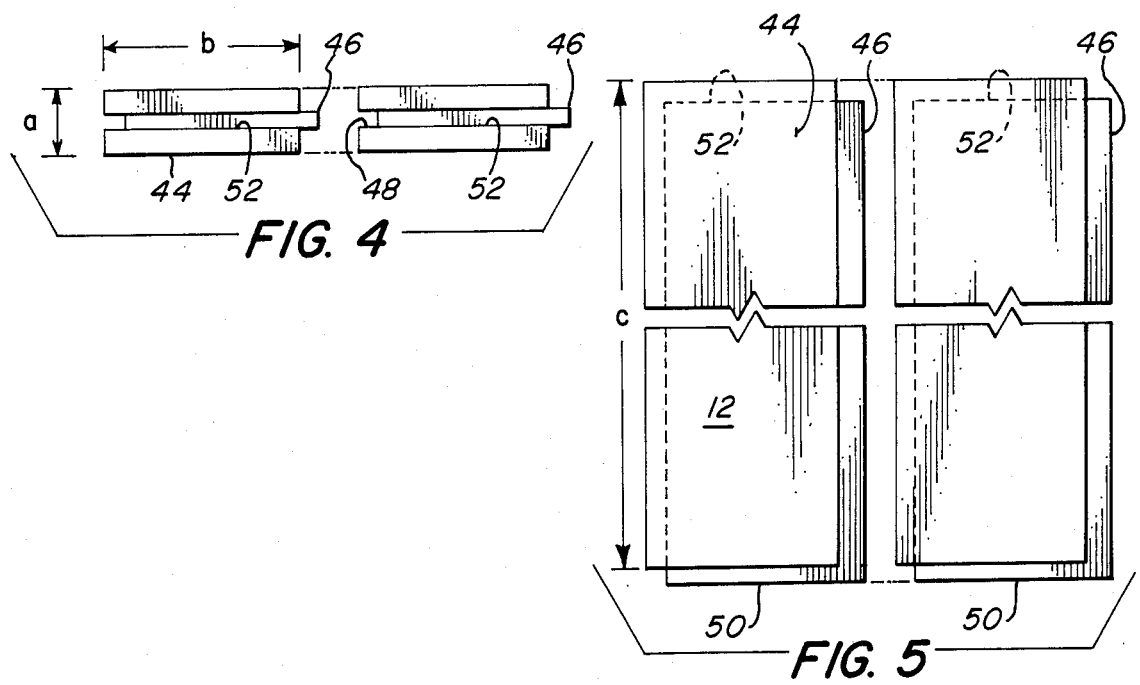

RESOURCE RECOVERY UTILITY

BACKGROUND OF THE INVENTION

This invention relates to an improved resource recovery utility. More particularly, this invention relates to an improved resource recovery utility based upon an enclosed sanitary landfill.

Many muncipalities use sanitary landfills as a means of waste disposal. In most localities, however, the volume of refuse is exceeding the availability of disposal sites necessitating the use of sites which are located at points quite distant from the municipality, resulting in substantially increased costs in transporting and handling the refuse.

Both state and local governmental agencies have imposed severe restrictions on sanitary landfill operations due to the noxious odors, rodents and potential damage due to the accumulation of gases, such as methane, usually associated therewith. In addition to these factors, the size and volume of landfills is restricted in an effort to control the leachate emanating therefrom and thereby reduce potential pollution of nearby water sources and habitable areas through ground water discharge. As a result, once a landfill is "filled", it is either sealed in some relatively impervious fashion (see, for example, U.S. Pat. No. 4,483,641) or is reclaimed into parks or other recreational areas (see, for example, U.S. Pat. No. 3,705,851).

SUMMARY OF THE INVENTION

It is an object of the present invention to provide an expandable landfill which can be substantially expanded beyond present volume limits without increasing the amount of leachate emanating therefrom and, in fact, controlling, reducing and even eliminating leachate discharge.

It is another object of the present invention to provide a resource recovery utility whereby the landfill can be continuously employed as a source of energy in the form of steam and/or pipeline gas.

It is a further object of the present invention to provide a reusable landfill which is environmentally acceptable and economically attractive.

It is still a further object of the present invention to provide a reusable landfill which functions as a resource recovery utility capable of generating and recovering sufficient energy to energize the recovery operation as well as electrical generators to provide a supplemental source of energy for the municipality or other energy sources.

These as well as other objects and advantages are provided by the resource recovery utility of the present invention which comprises:

(i) a landfill;
(ii) a continuous wall surrounding the perimeter of said landfill;
(iii) a containment structure extending completely over said landfill and affixed to said continuous wall;
(iv) means for introducing refuse into said landfill;
(v) means for compacting refuse;
(vi) means for removing and recoving methane generated by anaerobic bacterial digestion of organic materials contained in said refuse; and
(vii) means for removing at least a portion of the compacted refuse from said landfill.

BRIEF DESCRIPTION OF THE DRAWINGS

The present invention will become more readily apparent and understood upon consideration of the drawings wherein:

FIG. 3 is an exploded view of the landfill in elevation ilustrating the vertical expansion capability provided by the present invention;

FIG. 4 is a plan view illustrating one embodiment of the wall construction which surrounds the perimeter of the landfill; and FIG. 5 is an elevation view of the wall construction shown in FIG. 4.

DETAILED DESCRIPTION OF THE INVENTION

Figure 1:
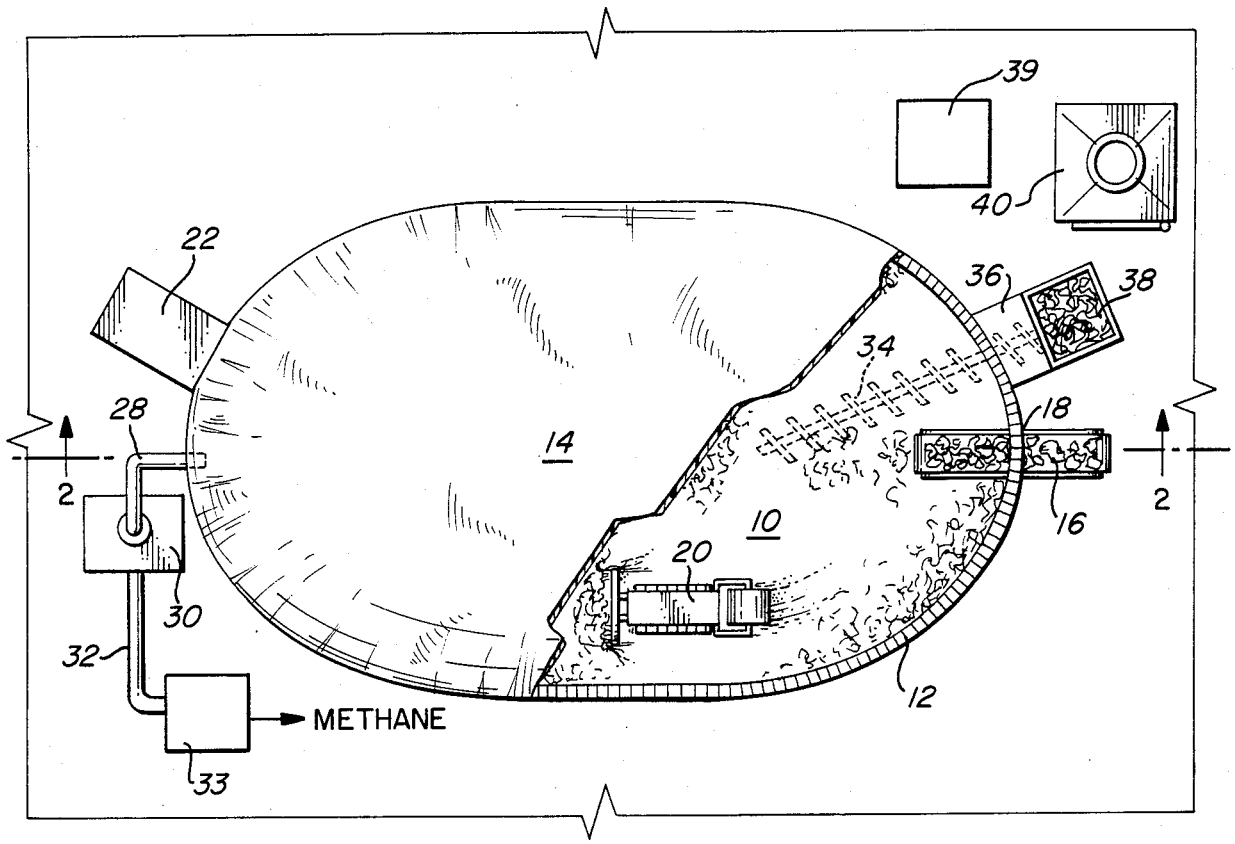
FIG. 1 is a plan view schematically illustrating one embodiment of the landfill of the present invention.
Figure 2:
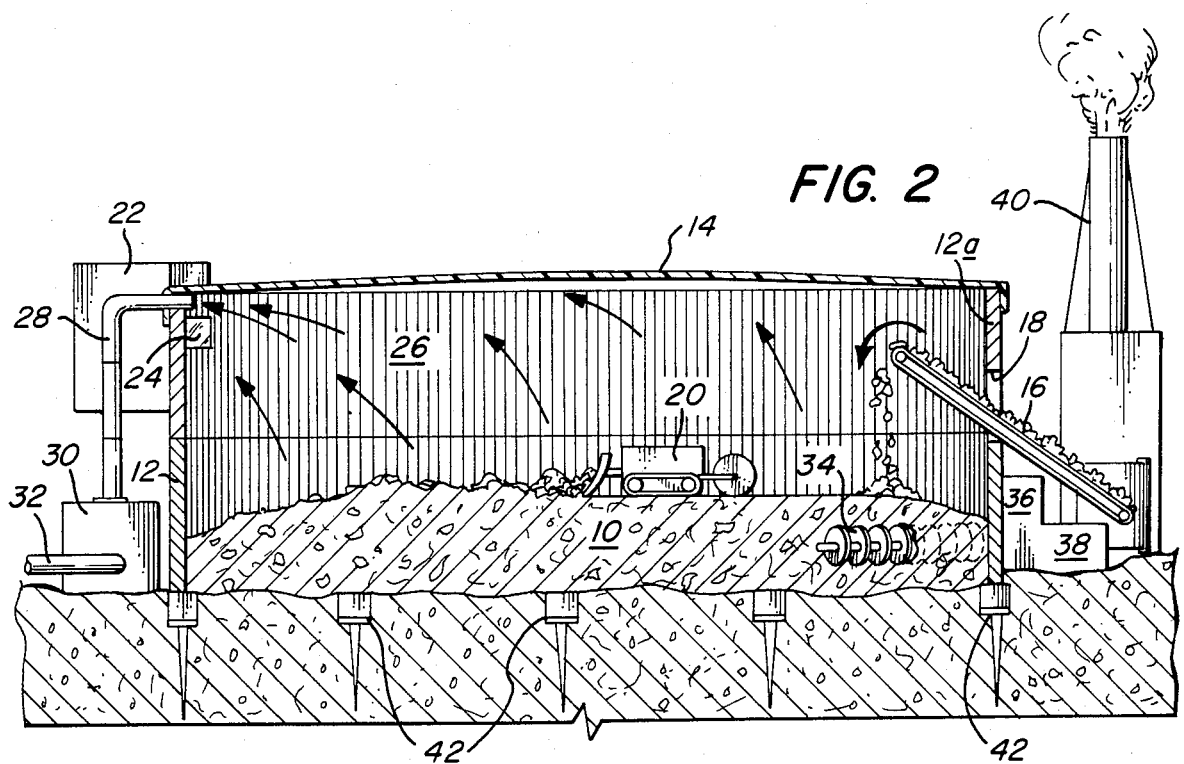
FIG. 2 is a cross sectional view of the land fill taken along line 2—2 in FIG. 1.

The present invention will now be described in detail with reference to the drawings. As shown in FIGS. 1 and 2, the perimeter of the landfill 10 is surrounded by a continuous wall 12. A containment structure or cover 14 extends completely over the landfill 10 and is affixed to the continuous wall 12 in any convenient manner. Means for introducing refuse into the landfill 10 can be conveniently provided by a conveyor belt 16 which provides a means of ingress for the refuse deposited thereon by garbage or dump trucks to the landfill 10 through an aperture 18 in the continuous wall 12. Means for compacting the refuse within the enclosed landfill of the present invention are provided by landfill compactors 20, vibratory rollers, or the like. The landfill compactor 20 can be operated by remote control by an operator in a control station 22 who can control the entire operation of the landfill 10 from the control station 22 which is affixed to the wall 12 and which provides visual access to the landfill 10 through window 24 in the wall 12.

Anaerobic digestion of organic waste materials in the compacted refuse in the landfill 10 produces a mixture of gases primarily comprising methane and carbon dioxide. It is desirable to recover the methane from the landfill for use as a fuel source. Also, it is desirable to remove the methane from the landfill since it represents a serious potential safety hazard in the event it seeps out of the landfill into a closed structure such as a building wherein it could combine with oxygen to form an explosive mixture.

The primary function of the containment structure or cover 14 which extends completely over the landfill is to contain the methane gas which is lighter than air in the vapor collection zone 26 above the landfill 10 formed by the continuous wall 12 and the cover 14. The methane is withdrawn from the vapor collection zone 26 through vent line 28 by pumping means 30 and is passed to a separation plant 33 via transfer line 32. The separation plant can produce high purity methane for use as a fuel by such methods as, for example, absorption of the carbon dioxide in a solvent (amine scrubbing) or adsorption of the carbon dioxide on a solid material (e.g., molecular sieves or activated carbon)—see, for example, U.S. Pat. No. 4,518,399.

If the compacted refuse has value for recycling purposes, at least a portion of such compacted refuse can be removed from the landfill 10 by suitable means such as an auger 34 or conveyer. The auger 34 is powered by an internal combustion engine contained in housing 36. The effluent compacted refuse removed from the landfill 10 is collected at transfer station 38 and then can be fed to an on-site combustion chamber 40 wherein it is oxidized and converted to energy in the form of steam. The thus obtained steam can be used for on-site heat exchange purposes or to drive a turbine/generator thereby generating electricity. Alternatively, the compacted refuse can be passed from transfer station 38 to an encapsulating plant 39 wherein the compacted effluent can be encapsulated in a stable material and thereby converted into useful construction materials (see, for example, U.S. Pat. Nos. 3,442,498; 4,018,679 and 4,306,978). The combustion chamber 40 oxidizes the compacted refuse to steam, carbon monoxide, carbon dioxide, and ash. The steam is recovered and utilized as described hereinabove. The levels of carbon monoxide and carbon dioxide obtained can be safely vented to the atmosphere. The ash can either be recycled to the landfill or sent to an encapsulating plant as described herein.

Normally, landfill sites are below grade areas such as abandoned quarries, gravel pits, swamps or other wetland areas. In order to stabilize the base of a wetlands landfill site, pilings or other supports 42 are first driven into the ground as shown in FIG. 2. Thereafter, the landfill is generated and compacted on top of the stabilized base. In the present invention, since the resource recovery utility is constructed as a fully enclosed vertical expansion of an existing landfill, the "footprint" of the leachate discharge does not change. Leachate discharge is not increased and will be confined to the existing footprint. In fact, the footprint can be attenuated because the flow of water that enters and exits the system can be controlled by the operator. The entire site is encompassed by the continuous vertical wall 12 which, together with the containment structure 14, contains the leachate, litter and odors and keeps out rodents. These factors are the most objectionable facets normally associated with a landfill. Thus, the improved landfill of the present invention provides enhanced environmental and aesthetic acceptability.

In operation, once the landfill is "filled" by normal state and/or municipal standards, the continuous vertical wall 12 of the present invention can be easily and economically erected around the perimeter thereof. The wall 12 is erected from panels, one embodiment of which is shown in FIGS. 4 and 5, having overall tongue 46 and 50 and groove 48 and 52 construction. The panels can be of any size which can be conveniently handled for example, the dimensions a, b and c in FIGS. 4 and 5 can range from a=4–6 inches, b=6–12 inches, and c=5–10 feet. The overall tongue and groove construction enables the panels to be readily erected in side by side fashion around the entire perimeter of the landfill. Thereafter, adjacent panels can be held together with appropriate bracing to withstand the pressure of the landfill. In this fashion, a 10 foot wall, for example, can be readily erected around the perimeter of the "filled" landfill, for a ten acre landfill, thereby creating a vertical expansion of the landfill which can accommodate about an additional 64,500 tons of refuse. The continuous wall can be expanded vertically, with appropriate structural supports as shown in FIG. 3. The wall 12 can be raised by annular wall segments 12a, 12b, 12c, 12d and the like as required over a period of time. Because of the operator control of the water content of the landfill afforded by the continuous containment structure 14, the footprint of the original landfill does not change but a huge increase in the volume of refuse at that one landfill site is achieved.

The containment structure 14 can be fabricated from a geofabric such as that manufactured by Staff Engineering of Fairfield, Conn. and Montclair, N.J. and sold under the trademark HYPALON. Alternatively, the cover 14 can be any conventional light weight roof system which can be adapted to contain methane gas.

In accordance with the present invention, the methane gas obtained from the methane separation plant can be utilized as an energy source to power the resource recovery utility. It is believed that a surplus of methane over that required to run the resource recovery utility will be available as a marketable commodity. The methane gas obtained is of "pipeline" quality and has sufficient B.T.U. content to energize internal combustion engines. These internal combustion engines can be employed as sources of power to energize the resource recovery utility as well as electrical generators to energize the adjoining municipality. Moreover, the steam generated from the combustion of the compacted refuse can also be used to generate power and/or electricity.

Thus, the present invention provides a reusable landfill which provides means for recovery of our natural resources and functions as an essentially independent utility plant in an economical and environmentally acceptable fashion.

Although the foregoing discussion has focused on relatively large landfills, the present invention, on a scaled-down basis, can similarly be employed for home use wherein the waste effluent from a house is discharged to a mini-enclosed landfill as described herein situated in a far corner of the back yard with sufficient power generating potential to supply the energy needs of that house.

What is claimed is:

1. A resource recovery utility comprising:
   (i) a landfill;
   (ii) a continuous wall surrounding the perimeter of said landfill;
   (iii) a containment structure extending completely over said landfill and affixed to said continuous wall;
   (iv) means for introducing refuse into said landfill;
   (v) means for compacting said refuse;
   (vi) means for removing and recovering methane generated by anaerobic bacterial digestion of organic materials contained in said refuse; and
   (vii) means for removing at least a portion of the compacted refuse from said landfill.

2. A resource recovery utility defined in claim 1 wherein the means for introducing refuse into the landfill is a conveyor belt extending through an aperature in the continuous wall thereby providing a means of ingress for refuse deposited thereon to the landfill.

3. A resource recovery utility as defined in claim 1 wherein the compacted refuse removed from the landfill is transferred to an encapsulating plant wherein the compacted refuse is encapsulated in a stable material.

4. A resource recovery utility as defined in claim 1 wherein the landfill is stabilized on pilings.

5. A resource recovery utility as defined in claim 1 wherein the containment structure is formed from a geofabric.

6. A resource recovery utility as defined in claim 1 wherein the containment structure is a light weight roof system.

7. A resource recovery utility as defined in claim 1 wherein the methane gas and/or steam recovered from the resource recovery utility is/are used as a source of energy to operate the resource recovery utility.

8. A resource recovery utility as defined in claim 1 wherein a vapor collection zone is formed in the volume defined above the landfill and between the continuous wall and the containment structure affixed thereto.

9. A resource recovery utility as defined in claim 8 wherein a mixture of methane and carbon dioxide is withdrawn from the vapor collection zone through a vent line in the containment structure by pumping means and passed via a transfer line to a separation plant wherein high purity methane is recovered.

10. A resource recovery utility as defined in claim 1 wherein at least a portion of the compacted refuse is removed from the landfill by an auger or conveyor located beneath the surface of the compacted refuse and extending through the continuous wall.

11. The resource recovery utility as defined in claim 10 wherein the compacted refuse removed from the landfill is fed to a combustion chamber and oxidized to generate steam.

12. A resource recovery utility as defined in claim 1 wherein the vertical height of the continuous wall can be increased by stacking one or more additional continuous wall structures on top of the initial continuous wall.

13. A resource recovery utility as defined in claim 12 wherein each of the continuous walls is formed from a plurality of panels, each having a tongue and groove structure on the opposed horizontal and vertical sides thereof.

14. A resource recovery utility as defined in claim 1 wherein the means for compacting the refuse is a landfill compactor.

15. A resource recovery utility as defined in claim 14 additionally containing a control station adjacent the continuous wall, said continuous wall having a window therein permitting an operator in said control station to have visual access to the landfill.

16. A resource recovery utility as defined in claim 15 wherein the landfill compactor is operated by said operator by remote control.

* * * * *